United States Patent
Kozikowski

Patent Number: 5,391,744
Date of Patent: Feb. 21, 1995

[54] COCAINE ANALOGS

[75] Inventor: Alan P. Kozikowski, Ponte Vedre Beach, Fla.

[73] Assignee: Mayo Foundation For Medical Education and Research, Rochester, Minn.

[21] Appl. No.: 118,140

[22] Filed: Sep. 8, 1993

Related U.S. Application Data

[62] Division of Ser. No. 949,461, Sep. 22, 1992, Pat. No. 5,268,480.

[51] Int. Cl.$^6$ .............. C07F 7/02; C07F 9/40; C07D 451/12
[52] U.S. Cl. ...................... 546/23; 546/14; 546/124
[58] Field of Search .............. 546/124, 23, 14; 514/63, 80, 304

[56] References Cited

PUBLICATIONS

M. C. Ritz et al., *Science*, 237, 1249 (1987).
J. Bergman et al. *J. Pharmacol. Exp. Ther.*, 251, 150 (1989).
R. L. Carke et al., *J. Med. Chem.*, 16, 1260 (1973).
F. I. Carroll et al., *J. Med. Chem.*, 34, 2719 (Sep. 1991).
F. I. Carroll et al., *J. Med. Chem.*, 35, 969 (1992).
S. J. Yi et al., *Neuropharmacol.*, 29, 475 (1990).
J. A. Javitch et al., *Mol. Pharmacol.*, 26, 35 (1985).
A. P. Kozikowski, *Med. Chem. Res.*, 1, 312 (1991).

*Primary Examiner*—Alan L. Rotman
*Attorney, Agent, or Firm*—Schwegman, Lundberg & Woessner

[57] ABSTRACT

Bioactive cocaine analogs of the general formulae:

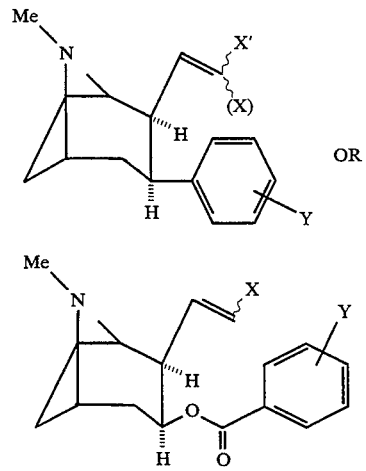

are provided wherein X' is H or $(C_1-C_5)$alkyl, X is H, halo, alkyl, alkoxy, perfluoroalkyl, nitro, alkoxycarbonyl, dialkoxyphosphonyl, acyl, perfluoroacyl, azido (substituted)silyl or (substituted)thio, and Y is H, halo, nitro, amino or (substituted)amino, alkoxycarbonyl, carboxy, alkyl or alkoxy; and the pharmaceutically acceptable salts thereof.

11 Claims, No Drawings

COCAINE ANALOGS

This is a division of application Ser. No. 07/949,461, filed Sep. 22, 1992, now U.S. Pat. No. 5,268,480.

BACKGROUND OF THE INVENTION (R)-Cocaine or (−)-cocaine (1) is a plant alkaloid purified from the leaves of Erythroxylon coca and has been a subject of scientific investigation since the late 1800s. It is one of the eight possible stereoisomeric forms of methyl 3- (benzoyloxy) -8-methyl-8-azabicyclo [3.2.1 ]octane-2 carboxylate.

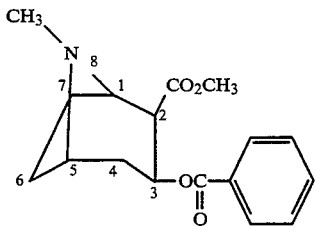

1

In both animals and humans, cocaine is one of the most reinforcing drugs known, which has given rise to a serious cocaine abuse epidemic in the United States over the last 10–15 years. See, D. F. Musto, *Opium, Cocaine and Marijuana in American History, Sci. Amer.*, 256, 40 (1991); D. Clouet et al., eds., "Mechanisms of Cocaine Abuse and Toxicity," *NIDA Research Monograph* (1988) at page 88; C. E. Johanson et al., *Pharmacol. Rev.*, 41, 3 (1989).

Cocaine has many physiological effects. It is a local anesthetic, and this property is responsible for its early legitimate use in medicine. However, many newer compounds have been developed that are superior to cocaine for this purpose. Cocaine is also a powerful vasoconstrictant and as such has some current use in medicine during nasal or throat surgery where control of bleeding is desired. Cocaine also has very potent effects on the sympathetic nervous system, and it is well know to increase heart rate and blood pressure. From the point of view of drug abuse, the most relevant effects of the drug include its ability to produce euphoria and its reinforcing documented in human subjects. See, R. R. Griffiths et al., in *Advances in Substance Abuse*, Vol. 1, N.K. Mello, ed., UAI Press Inc., Greenwich, Conn. (1980) at pages 1–90. In addition to being a powerful reinforcer, cocaine also has properties common to other drugs subject to abuse. For example, tolerance occurs to some of its effects, and its psychological withdrawal syndrome takes place over a long time period, which includes periods of craving during which relapse to drug use may often occur. See, F. H. Gawin et al., *Arch. Gen. Psychiatry*, 43., 107 (1986).

Over the past 10 years, there have been significant advances in understanding the mechanism of action of cocaine. The development of drug self-administration as a useful animal model for reinforcing properties has led to exploration of many of the physiological, neurochemical, neuroanatomical, and pharmacological correlates. See, R. R. Griffiths, cited above.

Several studies have shown that cocaine binds to the dopamine transporter and inhibits dopamine transport (M. J. Kubar et al., in "Mechanisms of Cocaine Abuse and Toxicity", D. Clouet et al., eds., *NIDA Research Monograph* (1988) at pages 14–22). In addition, drugs that are potent in maintaining self-administration such as nomifensine, methylphendiate and mazindol, are also potent inhibitors of binding at the transport site for dopamine, whereas compounds that are weak in self-administration studies are correspondingly weak inhibitors of the binding site. For example, M. C. Ritz et al., in *Science*, 237, 1249 (1987), showed that the relative ability of several compounds to displace [$^3$H]mazindol binding to the dopamine transporter from rat striatum was correlated to drug self-administration studies in nonhuman primates. Similarly, J. Berman et al., *J. Pharmacol. Exp. Ther.*, 251, 150 (1989), found a good correlation between displacement of [$^3$H]-cocaine binding to the transporter and drug self-administration behavior in squirrel monkeys. The most potent compounds in binding and behavioral studies reported from both investigations were 3β-phenyltropane-2β-carboxylic acid methyl ester (1a, WIN-35,065-2) and 3β-(p-fluorophenyl)tropane-2β-carboxylic acid methyl ether (1b WIN-35,428), the so-called "WIN compounds" reported originally by R. L. Clark et al., *J. Med. Chem.*, 16, 1260 (1973).

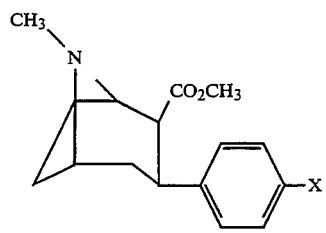

1a X = H
1b X = F

Only a limited number of cocaine analogs have been available to study the structural requirements for binding to the dopamine transporter and for cocaine-like reinforcing properties. For example, F. I. Carroll et al., *J. Med. Chem.*, 34, 2719 (Sept. 1991); *Eur. J. Pharm.*, 184, 329 . (1990) synthesized and measured the binding affinity of a number of new 3β-(p-substituted phenyl)-tropane-2β-carboxylic acid methyl esters, and measured their ability to inhibit the binding of 0.5 nM [$^3$H]-1b to the dopamine transport site of rat striata. Compound 1c, X=I was found to have a potency 78 times greater than (−)-cocaine (1), while compound 1d (X=Cl) had a potency 85 times that of cocaine in this in vitro assay. F. I. Carroll et al., in *J. Med. Chem.*, 35, 969 (1992) went on to propose that specific hydrogen bond donor groups are present within the cocaine recognition site which bind to the 2-carbomethoxy group.

However, a need exists for analogs of cocaine that exhibit enhanced analgesic and/or vasoconstrictive properties, and which are potentially more selective than (−)-cocaine. A further need exists for cocaine analogs which can be employed to further characterize the cocaine binding site(s), to assist the development of specific cocaine binding site agonists and antagonists.

SUMMARY OF THE INVENTION

The present invention provides bioactive analogs of (−)-cocaine of formula A:

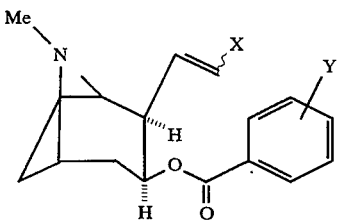

wherein X is H, halo [F, Cl, Br, I], $(C_1-C_5)$alkyl, $(C_1-C_5)$alkoxy, $(C_1-C_5)$perfluoroalkyl, $(C_2-C_6)$acyl, $(C_2-C_6)$perfluoroacyl, nitro $(NO_2)$, $(C_1-C_5)$alkoxycarbonyl, azido, $Si(R)_3$, SR or $P(O)(OR)_2$, wherein R is H, $(C_1-C_5)$alkyl or $(C_6-C_{12})$aryl; and Y is H, halo, $NO_2$, $NR_2$ wherein each R is as defined above, $(C_1-C_5)$alkoxycarbonyl, carboxy $(-CO_2H)$, $(C_1-C_5)$alkyl or $(C_1-C_5)$alkoxy; and the pharmaceutically acceptable salts thereof.

The present invention also provides bioactive analogs of (−)-cocaine of formula B:

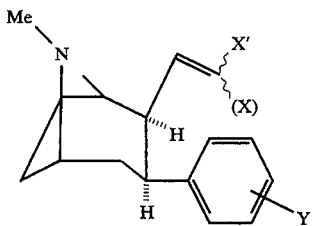

wherein X' is H, $(C_1-C_5)$alkyl or halo, wherein X and Y are as defined above, and the pharmaceutically acceptable salts thereof.

Preferably, X and Y are H or halo and X' is H or $(C_1-C_5)$alkyl. Preferably, Y is in the 4'- or para-position on the phenyl ring. Most preferably, Y is Cl.

Although the compounds of formulas A and B do not possess a $C_2$ substituent capable of acting as a hydrogen bond acceptor for the H-bond donor group which has been posited to be present at the cocaine binding site, they were unexpectedly found to exhibit a high binding affinity for the dopamine transporter of rat striatal membranes. For example, the cocaine analog of formula A, wherein X is $CO_2Et$ and Y is H was about 4–5 times more potent than cocaine in displacing [$^3$H]mazindol binding from the receptor site and in inhibiting high-affinity uptake of [$^3$H]dopamine into striatal nerve endings. The compound of formula B wherein X is H and Y is 4'-Cl was at least twenty-fold more potent than cocaine in vivo and at least twice as long-acting. Thus, the compounds of the invention would be expected to possess potent anesthetic, and/or vasoconstrictive properties.

In formulas A and B, a waved line indicates a bond that can be either syn or anti with respect to the $C_2$—CH= bond. Broken lines indicate bonds that are anti to the $NCH_3$ group.

The compounds of formulas A and B also include the pharmaceutically acceptable salts thereof, i.e., the acid addition salts of the methylamino group such as the hydrochloride, hydrobromide, methosulfate, sulfate, tartrate, fumarate, citrate, malate and the like.

As used herein, the term "$(C_1-C_5)$alkyl" or "$(C_1-C_5)$perfluoroalkyl" includes straight- or branched-chain alkyl and also includes $(C_3-C_5)$cycloalkyl or $(C_3-C_5)$perfluorocycloalkyl. The term $(C_6-C_{12})$aryl includes $(C_7-C_{12})$alkylaryl or $(C_7-C_{12})$aralkyl. Preferably, alkyl is $CH_3$ or $CH_2-CH_3$; perfluoroalkyl is $CF_3$ or $C_2F_5$, aryl is phenyl, tolyl, benzyl or phenethyl; alkoxy is methoxy or ethoxy and $(C_1-C_5)$alkoxycarbonyl is ethoxycarbonyl or methoxycarbonyl.

DETAILED DESCRIPTION OF THE INVENTION

I. Synthesis

As shown in Scheme 1, the vinyl compounds 2a and 2b were synthesized readily from the unstable aldehyde 4, a compound obtained by Swern oxidation of the alcohol 3. Alcohol 3 which is available in optically pure form from (−)-cocaine, wherein the following reaction conditions are employed: (a) conc. $H_2SO_4$, MeOH, reflux, 18 hr; (b) (t-butyl)(dimethyl)silylchloride, imidazole, 25° C., 20 hr; (c) diisobutylaluminum hydride, $CH_2Cl_2$, 78° C., 4 hr and (d) Swern oxidation. After the Wittig reaction of 4, using $CH_2=PPh_3$ or $ClCH=PPh_3$, the silyl group is cleaved by the action of fluoride ion, and the free hydroxyl group was then benzoylated (PhCOCl, pyridine) to yield 2a or 2b.

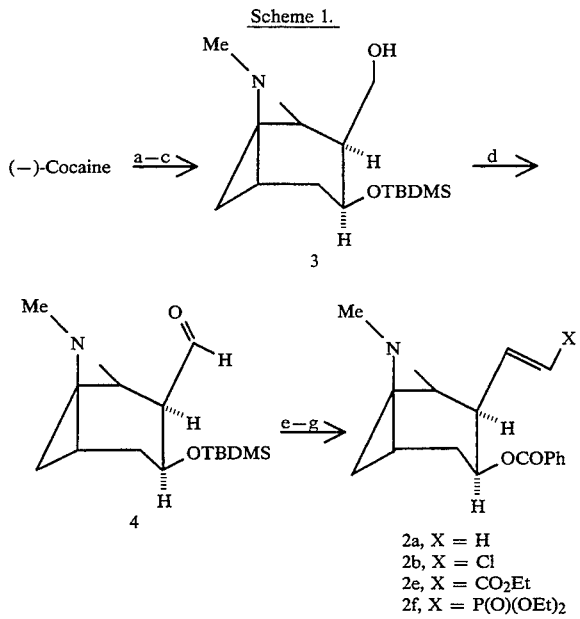

Scheme 1.

The Wittig reaction of compound 4 with reagents of the general formula $XCH=PPh_3$, or Wadsworth-Emmons reaction employing reagents of the formula $XCH-P(O)(OR)_2$, followed by desilylation and benzoylation with $YPhCOCl$ provides a general route to compounds for formula A, wherein X is halo, $(C_1-C_5)$alkyl, $(C_1-C_5)$perfluoroalkyl, $(C_1-C_5)$alkoxycarbonyl, $(C_2-C_6)$acyl, $NO_2$ and the like. The use of condensation procedures (e.g., aldol or Henry reaction) followed by dehydration, also provides routes to the compounds of the invention.

For example, aster 2e, wherein X is $CO_2Et$ was readily prepared from adehyde 4 by a two-step sequence involving Wittig reaction with (carboethoxymethylene)triphenylphosphorane, followed by desilylation and benzoylation. The phosphonate 2f (X=$P(O)(OEt)_2$) was prepared by the Wadsworth-Emmons protocol using the anion derived from tetraethyl methylenediphosphonate.

The conjugate addition of Grignard reagents of the general formula YPhMgBr to anhydroecgonine methyl ester, followed by conversion of the 2-CO$_2$Me group to the aldehyde and conversion of the aldehyde group to the corresponding olefin, —CH=C(X)(X'), by Wittig reaction provides a general route to compounds of formula B. For example, as shown in Scheme 2, to obtain compound 2c and 2d, p-chlorophenylmagnesium bromide was added to anhydroecgonine methyl ester (5) as described by F. I. Carrol et al., in *J. Med. Chem.*, 34, 2719 (1991). The 3β-substituted isomer was separated from the 3α-isomer, and the ester converted to aldehyde in two steps by reduction to alcohol followed by Swern oxidation. Lastly, reaction of this aldehyde with methylenetriphenylphosphorane or chloromethylenetriphenylphosphorane gave the vinyl analogs 2c and 2d.

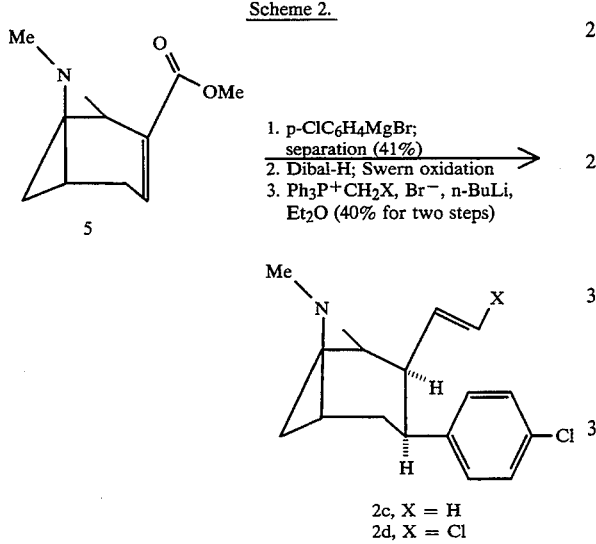

Scheme 2.

1. p-ClC$_6$H$_4$MgBr; separation (41%)
2. Dibal-H; Swern oxidation
3. Ph$_3$P$^+$CH$_2$X, Br$^-$, n-BuLi, Et$_2$O (40% for two steps)

2c, X = H
2d, X = Cl

II. Biological Results

A. Pharmacological Results

The six new analogs were tested for their ability to displace [$^3$H]mazindol binding from rat striatal membranes as well as to inhibit high-affinity uptake of [$^3$H]dopamine into striatal nerve endings (synaptosomes) in accordance with protocols described previously by S.-J. Yi et al., *Neuropharmacol.*, 29, 475 (1990); J. A. Jayitch et al., *Mol. Pharmacol.*, 26, 35 (1984), and M. C. Ritz et al., *Science*, 237, 1219 (1987). These data are presented in Table I. Additionally, for comparison purposes, data are presented for (−)-cocaine and for 3β-(p-chlorophenyl)tropane-2β-carboxylic acid methyl ester (1d).

TABLE I

Dopamine Uptake and Mazindol Binding of Cocaine Analogs 2a–2f and 6.

| Compound | IC$_{50}$ (μM) [$^3$H] Mazindol Binding mean ± SE (N) | IC$_{50}$ (μM) [$^3$H] Dopamine Uptake mean ± SE (N) |
|---|---|---|
| (−)-cocaine | 0.58 ± 0.07 | 0.57 ± 0.18 |
| 2a | 1.73 ± 0.54 (3) | 1.12 ± 0.39 (4) |
| 2b | 0.222 ± 0.049 (7) | 0.368 ± 0.19 (4) |
| 2c | 0.0012 ± 0.0003 (5) | 0.0032 ± 0.0006 (3) |
| 2d | 0.00072 ± 0.00006 (3) | 0.00126 ± 0.0003 (3) |
| 2e | 0.05 ± 0.01 | 0.31 ± 0.01 |
| 2f | 4.85 ± 0.47 | 5.5 ± 0.07 |
| 1d | 0.0017 ± 0.0001 (3) | 0.0032 ± 0.0001 (3) |

As is apparent from the data of Table I, the vinyl analog 2a of cocaine is not substantially less active than the parent structure; in the dopamine uptake experiment, it is only two-fold less potent. By appending a chlorine atom to the β-position of the vinyl group, one obtains an analog 2b which in the mazindol binding assay is about two-fold more potent than cocaine.

Compounds 2c and 2d bind with affinities which are 480- to 800-fold higher than that of cocaine, but unlike cocaine or, in part, compound 1d, they will not be subject to the action of esterases in vivo. Consequently, the duration of action of such compounds is expected to be longer than that of cocaine analogs which retain one or both ester bonds. Analogs like 2c and 2d may therefore be useful in surgical applications to reduce bleeding or be used in studies which require chronic drug treatment in order to achieve a measurable endpoint. Additionally, these analogs might also offer certain advantages in the preparation of stable, radiolabeled ligands for use in PET or SPECT imaging studies, such as those described by F. I. Carroll et al., *J. Med. Chem.*, 35, 969 (1992). The present compounds may also be useful as markers for nociception in the central nervous system, as determined, for example, by spectral magnetic resonance imaging (MRI).

Compound 1d exhibited IC$_{50}$s of 1.7 nM in this mazindol binding study and 3.2 nM in the dopamine uptake study. Compound 2c is thus slightly more potent than its ester counterpart 1d.

Ester 2e was found to be about 4–5 times more potent than cocaine in both assays, while phosphonate analog 2f was also found to inhibit dopamine uptake, but was about 10 times less potent than cocaine.

III. Drug Discrimination Studies

The results of substitution and temporal tests conducted in rats trained to discriminate cocaine (10 mg/kg) from saline using a standard two-lever, water-reinforced FR 20 drug discrimination task are presented in Table II and Table III. The apparatus and general procedure are described hereinbelow, and follow those developed by P. Callahan et al., *Psychopharmacol.*, 103, 50 (1991).

TABLE II

Results of Cocaine Dose-Response and Temporal Tests in Animals Trained to Discriminate Cocaine (10 mg/kg) from Saline.

| Treatment | Dose (mg/kg) | Injection interval (min) | % Drug responses[a] | Rate[b] (responses/ min) | n/N[c] |
|---|---|---|---|---|---|
| A. Dose-response tests | | | | | |
| 1. Cocaine | | | | | |
| | 0.625 | 15 | 6 ± 2 | 27.3 ± 5 | 7/7 |
| | 1.25 | | 44 ± 18 | 21.3 ± 5 | 7/7 |
| | 2.5 | | 61 ± 16 | 31.6 ± 16 | 7/7 |

TABLE II-continued

Results of Cocaine Dose-Response and Temporal Tests in Animals Trained to Discriminate Cocaine (10 mg/kg) from Saline.

| Treatment | Dose (mg/kg) | Injection interval (min) | % Drug responses[a] | Rate[b] (responses/ min) | n/N[c] |
|---|---|---|---|---|---|
| | 5.0 | | 98 ± 2 | 89.0 ± 16 | 7/7 |
| | 10.0 | | 99 ± 1 | 75.8 ± 13 | 7/7 |
| ED50 = 1.7 mg/kg | | | | | |
| 2. Saline control | | 15 | 9 ± 1 | 27.6 ± 4 | 7/7 |
| B. Temporal tests | | | | | |
| 1. Cocaine | | | | | |
| | 10.0 | 5 | 85 ± 13 | 28.2 ± 8 | 7/7 |
| | | 15 | 99 ± 1 | 75.8 ± 13 | 7/7 |
| | | 30 | 100 | 60.6 ± 11 | 7/7 |
| | | 60 | 81 ± 14 | 23.0 ± 4 | 7/7 |
| | | 120 | 31 ± 18 | 27.7 ± 7 | 7/7 |

[a]Mean percentage of cocaine-appropriate responses (±S.E.M.) during the test session.
[b]Mean number of responses per min (±S.E.M.) prior to completion of the first FR 20 observed during the test session
[c]n/N: number of animals (n) completing 20 responses on either level out of the number of animals tested (N).

As demonstrated by the data summarized on Table II, the percentage of drug-appropriate responding after various doses of cocaine (0.625–10 mg/kg) increased in a dose-dependent manner. The dose of cocaine predicted to engender 50% cocaine-lever responding (ED50) was 1.7 mg/kg. Response rates were fairly stable across all test doses of cocaine. Administration of cocaine (10 mg/kg) following different injection intervals (5–120 min) indicated that an injection period of 5 min elicited a complete cocaine-like response which lasted for approximately 60 min. Cocaine given at a 120 min injection period elicited primarily saline-appropriate responding.

TABLE III

Results of Substitution Tests with 2c Following Different Injection Intervals in Animals Trained to Discriminate Cocaine (10 mg/kg) from Saline.[a]

| Treatment | Dose (mg/kg) | Injection interval (min) | % Drug responses[a] | Rate[b] (responses/ min) | n/N[c] |
|---|---|---|---|---|---|
| 2c | 0.05 | 30 | 19 ± 4 | 29.6 ± 9 | 7/7 |
| | 0.1 | | 40 ± 17 | 37.1 ± 6 | 7/7 |
| | 0.2 | | 83 ± 10 | 26.2 ± 6 | 7/7 |
| | 0.4 | | 99 ± 1 | 52.8 ± 9 | 7/7 |
| | 0.8 | | 93 ± 5 | 33.5 ± 9 | 7/7 |
| (ED$_{50}$ 0.11 mg/kg) | | | | | |
| 2c | 0.05 | 120 | 22 ± 14 | 18.4 ± 6 | 7/7 |
| | 0.1 | | 75 ± 16 | 25.7 ± 5 | 7/7 |
| | 0.2 | | 100 | 46.8 ± 9 | 7/7 |
| | 0.4 | | 72 ± 28 | 24.9 ± 18 | 3/5* |
| | 0.8 | | 95 | 7.7 | 1/7* |
| (ED$_{50}$ 0.08 mg/kg) | | | | | |
| 2c | 0.05 | 240 | 14 ± 14 | 28.3 ± 5 | 7/7 |
| | 0.1 | | 61 ± 17 | 23.5 ± 4 | 7/7 |
| | 0.2 | | 98 ± 1 | 47.9 ± 10 | 7/7 |
| | 0.4 | | 91 ± 9 | 23.6 ± 18 | 4/5* |
| | 0.8 | | 100 | 39.1 ± 1 | 3/7* |
| (ED$_{50}$ = 0.09 mg/kg) | | | | | |

[a]See Table I for explanation of table headings.
*Administration of 2c induced an intense stereotypic response, and animals failed to complete the test session.

As shown by the data summarized on Table III, administration of 2c (0.05–0.8 mg/kg) engendered a dose-dependent substitution for the cocaine cue. The ED$_{50}$ predicted for 2c was 0.11 mg/kg following the 30 min injection period. Variation of the injection interval (30–240 min) indicated that 2c has a long duration of action. Administration of 0.2 and 0.4 mg/kg of 2c induced complete cocaine-line responding in all animals following the 30 min injection period. However, these doses induced intense stereotypy following the 120 and 240 min injection periods which resulted in behavioral disruption (i.e., the animals were unable to complete the FR 20 test session). Response rates were stable across the different test doses of 2c, with the exception of the highest dose (0.8 mg/kg) of 2c which reduced response rates possibly due to the observed stereotypy.

The data obtained from the drug discrimination studies and presented in Tables II and III further confirm that 2c is at least-twenty-fold more potent than cocaine-in vivo following intraperitoneal administration. Additionally, these data support the fact that 2c is at least twice as long acting as cocaine, and probably much more than this, based upon casual observation wherein the animals treated with 0.8 mg/kg of 2c were still hyperactive 24 hours following administration.

Overall, the present results fail to support the existence of alhydrogen bonding interaction between the receptor and the C$_2$-moiety. If a single hydrogen bond contributes about 3 kcal mol$^{-1}$ to the free energy of interaction of cocaine with its recognition site, then loss in a single hydrogen bonding interaction should lead to at least a 100-fold increase in the measured IC$_{50}$ value for mazindol binding. See, P. R. Andrews et al., *J. Med. Chem.*, 27, 1648 (1984). The three-fold increase in the IC$_{50}$ of (−)-cocaine is thus far less than anticipated. The approximate twofold higher affinity of 2b compared to cocaine is more likely due to the hydrophobic or dipole interaction contributed by the single chlorine atom rather than to hydrogen bonding, since chlorine is a relatively poor hydrogen-bond acceptor group.

Most informative is the comparison between compounds 2c and 1d. Compound 2c is slightly more potent than the "Win" type compound 1d in spite of the fact that an unfunctionalized vinyl group serves as the ester group surrogate. Hydrogen bonding is, of course, the strongest when it involves an interaction between a proton and an electronegative atom (N,O,F). Although a weak interaction between the double bond of the vinyl group of 2c and the putative H-bond donor group of the receptor could be postulated, such an interaction cannot explain the similar IC$_{50}$ values of 2c and 1d. The presence of the additional chlorine atom on the vinyl group of 2d further increases binding affinity, doubling the potency of 2drelative to 2c. Accordingly, it is unlikely that hydrogen bonding interactions are operative in the binding of cocaine to its recognition site on the dopamine transporter.

The invention will be further described by reference to the following detailed examples, wherein tetrahydrofuran and diethyl ether were distilled from sodium benzophenone ketyl prior to use. Toluene was distilled from calcium hydride prior to use. Methylene chloride was distilled from calcium hydride and stored over 4A molecular sieves. Triethylamine and pyridine were distilled from calcium hydride and stored over potassium hydroxide pellets. Solvents used for extraction and chromatography were purchased in 5-gal drums, redistilled from an all glass apparatus, and stored in glass bottles. Silica gel 60 (Merck 70–230 mesh ASTM or 230–400 mesh ASTM for flash chromatography) was used for column chromatography. Other reagents were used as supplied or purified as noted.

All reactions were carried out in oven or flame dried glassware under an argon atmosphere (balloon filled) with magnetic stirring unless noted otherwise. Solutions and liquids were delivered by syringe through rubber septa. Brine refers to a saturated sodium chloride solution.

Infrared spectra were recorded on a Mattson GALAXY 2020 spectrometer. $^1$H NMR spectra were taken at 300 MHz (Bruker AC-300) in CDCl$_3$. $^{13}$C NMR spectra were taken at 75.46 MHz (Bruker AC-300) in CDCl$_3$. Chemical shifts are reported in $\delta$ units with reference to CDCl$_3$ ($\delta=7.26$ ppm for $^1$H NMR and $\delta=77.09$ ppm for $^{13}$C NMR) as internal standards. Low resolution mass spectra were obtained on a Hewlett Packard 5971A mass selective detector at an ionizing potential of 79 eV. High resolution mass spectra were determined on a VG 7070E mass spectrometer. Optical rotations were measured on a Perkin-Elmer 241 polarimeter using a standard cell.

EXAMPLE 1

3$\beta$-(t-Butyldimethylsilyloxy)-2$\beta$-T(methoxycarbonyl)-tropane.

2$\beta$-Carbomethoxy-3$\beta$-hydroxytropane (304 mg, 1.43 mmol) was dissolved in 4 mL of dry DMF. Imidazole (208 mg, 3.01 mmol) and tert-butyldimethylsilyl chloride (345 mg, 2.29 mmol) were added, and the reaction mixture was stirred overnight. Water was then added, and the mixture was extracted with ether. The combined organic layers were washed with water and brine and dried over MgSO$_4$. The solvent was evaporated in vacuo, and the residue was chromatographed on silica gel half-saturated with ammonia using ethyl acetate as eluent to give 265 mg of the title compound (55% yield): IR (thin film) 2951, 2897, 2857, 1790, 1716, 1497, 1271, 1144, 1107, 837 cm$^{-1}$; $^1$H NMR (CDCl$_3$, 300 MHz) $\delta$3.91 (dt, 1H, J=11.1, 6.1 Hz), 3.67 (s, 3H), 3.45–3.35 (m, 1H), 3.25–3.17 (m, 1H), 2.75–2.68 (m,1H), 2.18 (s, 3H), 2.35–1.42 (m, 6H), 0.84 (s, 9H), 0.02 (s, 3H), 0.01 (s, 3H); $^{13}$C NMR (CDCl$_3$, 75.46 MHz) $\delta$171.4, 64.6, 64.4, 61.6, 54.0, 51.1, 41.2, 39.5, 28.2, 25.8, 25.2, 18.1, 6.6, 6.3; mass spectrum m/z 313 (M+), 256, 242, 182, 97, 82; HRMS (FAB) calcd for C$_{16}$H$_{32}$NO$_3$Si (MH+) 314.2143, found 314.2145.

EXAMPLE 2

3$\beta$-(t-Butyldimethylsilyloxy)-2$\beta$-(hydroxymethyl)tropane (3)

The TBDMS-protected compound of Example 1 (900 mg, 2.88 mmol) was dissolved in 12 mL of methylene chloride. The solution was cooled to $-78°$ C., and a 1 M solution of diisobutylaluminum hydride in hexanes (11.5 mL, 11.5 mmol) was added. The reaction mixture was stirred at $-78°$ C. for 4 hr. A saturated solution of K$_2$CO$_3$ was added to quench the reaction. -The aqueous layer was extracted with chloroform. The combined organic layers were washed with water and brine and dried over MgSO$_4$. The solvent was evaporated in vacuo, and the residue was chromatographed using methanol as eluent to give 650 mg of the title alcohol 3 (79% yield): IR (thin film) 3453, 2947, 2899, 2857, 1472, 1252, 1098, 837 cm$^{-1}$; $^1$H NMR (CDCl$_3$, 300 MHz) $\delta$ 4.12–3.85 (m, 3H), 3.45–3.37 (m, 1H), 3.21–3.17 (m, 1H), 2.22 (s, 3H), 2.20–1.50 (m, 8H), 0.88 (s, 9H), 0.04 (s, 6H); $^{13}$C NMR (CDCl$_3$, 75.46 MHz) $\delta$66.9, 65.7, 63.6, 61.5, 46.5, 41.2, 40.6, 26.0, 25.4, 18.3, 6.6, 6.3; mass spectrum, m/z 285 (M+), 228, 154, 126, 83; HRMS (FAB) calcd for C$_{15}$H$_{32}$NO$_2$Si (MH+) 286.2194, found 286.2215.

EXAMPLE 3

3$\beta$-(t-Butyldimethylsilyloxy)-2$\beta$-vinyl tropane.

A solution of DMSO (325 $\mu$L, 4.58 mmol) in 1.5 mL of methylene chloride was added to a solution of oxalyl chloride (200 $\mu$L, 2.29 mmol) in 5 mL of methylene chloride at $-78°$ C. The reaction mixture was stirred for 10 min, and a solution of 3 (567 mg, 1.99 mmol) in 3 mL of methylene chloride was added. Stirring was continued for an additional 30 min, and triethylamine (2.8 mL, 19.9 mmol) was added. The reaction mixture was stirred at $-78°$ C. for 5 min and then allowed to warm to 25° C. Water was added, and the aqueous layer was extracted with ether. The combined organic layers were washed with water and brine and dried over MgSO$_4$. The solvent was evaporated in vacuo, and the residue (4) was dissolved in 3 mL of ether.

To a suspension of methyltriphenylphosphonium bromide (627 mg, 1.76 mmol) in 10 mL of ether was added n-butyllithium (0.7 mL, 2.5 M in hexanes, 1.76 mmol) at 0° C. After stirring at 25° C. for 4 hr, the solution of the aldehyde product 4 from Swern oxidation of alcohol 3 (250 mg, 0.88 mmol) in 3 mL of ether was added. The reaction mixture was stirred at 25° C. overnight. Water was added, and the aqueous layer was extracted with methylene chloride. The combined organic layers were washed with water and brine and dried over MgSO$_4$. The solvent was evaporated in vacuo, and the residue was chromatographed (hexane:ethyl acetate=1:1) to give 166 mg (67% yield from alcohol 3) of the title product: IR (thin film) 2953, 2932, 2886, 2857, 1101, 897, 835, 774 cm$^{-1}$; $^1$H NMR (CDCl$_3$, 300 MHz) $\delta$6.23–6.11 (m, 1H), 5.10–4.97 (m, 2H), 3.92 (dt, 1H, J=11.0, 6.2 Hz), 3.20–3.15 (m, 1H), 3.15–3.00 (m, 1H), 2.35–2.25 (m, 1H), 2.17 (s, 3H), 2.10–1.40 (m, 6H), 0.85 (s, 9H), 0.01 (s, 6H); $^{13}$C NMR (CDCl$_3$, 75.46 MHz) $\delta$139.2, 115.0, 67.8, 65.7, 61.6, 52.6, 41.5, 39.9, 26.2, 26.0, 25.3, 18.4, 6.4, 6.3; mass spectrum, m/z 281 (M+), 224, 210, 150, 123, 97, 82; HRMS calcd for C$_{16}$H$_{31}$NOSi (M+) 281.2167, found 281.2181.

EXAMPLE 4

3$\beta$-(Benzoyloxy)-2$\beta$-vinyltropane (2a)

The product of Example 3 (166 mg, 0.059 mmol) was dissolved in 1 mL of THF. Tetrabutylammonium fluoride (158 $\mu$L, 1 M in THF, 0. 158 mmol) was added at 0° C. The reaction mixture was warmed to 25° C. and stirred for 6 hr. Water was added, and the aqueous layer was extracted with ethyl acetate. The combined organic layers were washed with water and brine and dried over MgSO$_4$. The solvent was evaporated in vacuo, and the residue was dissolved in 1.5 mL of methylene chloride. A small amount of DMAP was added as a catalyst, and then triethylamine (33 μL, 0.24 mmol) and benzoyl chloride (14 μL, 0.12 mmol) were added at 0° C. The reaction mixture was warmed to 25° C. and stirred for 4 hr. The solvent was evaporated in vacuo, and the residue was chromatographed (hexane:ethyl acetate=3:1) to give 50 mg of cocaine analog 2a (31% yield): $[\alpha]^{22}{}_D=+5.18°$ (c=2.375), CH$_2$Cl$_2$); IR (thin film) 3070, 2940, 2880, 2849, 2799, 1718, 1277, 1115, 712 cm$^{-1}$; $^1$H NMR (CDCl$_3$, 300 MHz) δ 7.97 (d, 2H, J=7.4 Hz), 7.52 (t, 1H, J=7.4 Hz), 7.40 (t, 2H, J=7.3 Hz), 6.35–6.20 (m, 1H), 5.21 (dt, 1H, J=11.6, 6.4 Hz), 5.10–5.00 (m, 2H), 3.30–3.20 (m, 1H), 3.15–3.05 (m, 1H), 2.80–2.70 (m, 1H), 2.23 (s, 3H), 2.20–1.60 (m, 6H); $^{13}$C NMR (CDCl$_3$, 75.46 MHz) δ166.0, 137.7, 132.8, 130.7, 129.6, 128.3, 116.2, 69.0, 67.7, 61.4, 49.6, 41.4, 35.7, 26.0, 25.0; mass spectrum, m/z 271 (M+), 150, 105, 82; HRMS calcd for C$_{17}$H$_{21}$NO$_2$ (M+) 271.1567, found 271.1572.

EXAMPLE 5

3β-(t-Butyldimethylsilyloxy)-2β-[(E)-2-chlorovinyl]-tropane

By the procedure of Example 3, 311 mg (1.09 mmol) of alcohol 3 gave 180 mg (52% yield) of the title product (column chromatography, hexane:ethyl acetate=5:1): IR (thin film) 2953, 2857, 2886, 1489, 1251, 1132, 937, 837, 774 cm$^{-1}$; $^1$H NMR (CDCl$_3$, 300 MHz) δ6.26 (dd, 1H, J=13.3, 9.2 Hz), 5.92 (d, 1H, J=13.3 Hz), 3.90 (dr, 1H, J=11.0, 6.3 Hz), 3.15–3.05 (m, 1H), 3.05–2.95 (m, 1H), 2.45–2.35 (m, 1H), 2.17 (s, 3H), 2.10–1.40 (m, 6H), 0.85 (s, 9H), 0.01 (s, 6H); $^{13}$C NMR (CDCl$_3$) δ134.2, 117.1, 66.8, 65.4, 61.5, 50.5, 41.4, 39.9, 26.3, 25.9, 25.4, 18.2, 6.4, 6.3; mass spectrum, m/z 317 (M+, $^{37}$Cl), 315 (M+, $^{35}$Cl), 280, 184, 97, 82; HRMS calcd for C$_{16}$H$_{30}$NO$^{35}$ClSi 315.1778 (M+), found 315.1782.

EXAMPLE 6

3β-(Benzoyloxy)-2β-[(E)-2-chlorovinyl]tropane (2b)

By the same procedure used for the preparation of 2a, 180 mg (0.57 mmol) of the product of Example 5 gave 39 mg (22% yield) of compound 2b (column chromatography, hexane: ethyl acetate=2:1): $[\alpha]^{22}{}_D=-47.2°$ (c=1.925, CH$_2$Cl$_2$); IR (thin film) 3063, 2942, 2880, 2801, 1717, 1451, 1277, 1115, 939, 822, 712 cm$^{-1}$; $^1$H NMR (CDCl$_3$, 300 MHz) δ 7.97 (d, 2H, J=7.4 Hz), 7.55 (t, 1H, J=7.4 Hz), 7.43 (t, 1H, J=7.3 Hz), 6.42 (dd, 1H, J=13.4, 10.0 Hz), 5.93 (d, 1H, J=13.4 Hz), 5.19 (dt, 1H, J=11.4, 6.5 Hz), 3.30–3.20 (m, 1H), 3.15–3.05 (m, 1H), 2.85–2.75 (m, 1H), 2.22 (s, 3H), 2.20–1.60 (m, 6H); $^{13}$C NMR (CDCl$_3$, 75.46 MHz) δ166.0, 132.9, 130.4, 129.6, 128.4, 118.2, 68.6, 66.7, 61.4, 47.1, 41.3, 35.6, 26.1, 25.1; mass spectrum, m/z 307 (M+, $^{37}$Cl), 305 (M+, $^{35}$Cl), 270, 224, 184, 148, 105, 82, 77; HRMS calcd for C$_{17}$H$_{20}$NO$_2$$^{35}$Cl (M+) 305.1178, found 305.1170.

EXAMPLE 7

3β-(4-Chlorophenyl)-2β-vinyltropane (2c)

3β-(4-Chlorophenyl)tropane-2β-carboxylic acid methyl ester (250 mg, 0.85 mmol) was reduced to the corresponding alcohol by the procedure of Example 2. The alcohol was then oxidized to aldehyde, which was then transformed to the title product 2c (39.4 mg, 18% overall yield) according to the procedure of Example 3 (column chromatography using at first ethyl acetate, then ethyl acetate saturated with ammonia as eluent): $[\alpha]_D^{22}=-32.5°$ (c=1.97, CH$_2$Cl$_2$); IR (thin film) 3071, 2936, 2878, 2847, 2797, 1493, 1354, 1092, 1013, 818 cm$^{-1}$; $^1$H NMR (CDCl$_3$, 300 MHz) δ 7.21 (d, 2H, J=8.5 Hz), 7.04 (d, 2H, J=8.5 Hz), 6.10–5.90 (m, 1H), 4.82 (dd, 1H, J=10.3, 2.0 Hz), 4.70–4.60 (m, 1H), 3.40–3.30 (m, 1H), 3.20–3.10 (m, 1H), 3.04 (dt, 1H, J=13.2, 5.3 Hz), 2.26 (s, 3H), 2.40–1.50 (m, 7H); $^{13}$C NMR (CDCl$_3$, 75.46 MHz) 141.8, 138.9, 131.4, 129.3, 128.0, 115.6, 68.4, 62.0, 52.0, 42.1, 35.9, 34.5, 26.4, 25.0; mass spectrum, m/z 263 (M+, $^{37}$Cl), 261 (M+, $^{35}$Cl), 206, 128, 97, 82; HRMS calcd for C$_{16}$H$_{20}$N$^{35}$Cl (M+) 261.1280, found 261.1280.

EXAMPLE 8

3β-(4-Chlorophenyl)-2β-[(E)-2-chlorovinyl]tropane (2d)

A solution of butyllithium (0.32 mL, 2.5 M in hexane, 0.68 mmol) was added to a stirred solution of chloromethyltriphenylphosphonium chloride (237 mg, 0.68 mmol) in dry Et$_2$O (5 mL) at room temperature under N$_2$ atmosphere. The resulting orange mixture was stirred for 30 min at that temperature, and then crude 3β-(4-chlorophenyl)-2β-formyltropane (60 mg, 0.23 mmol) in dry ether (4 mL) was added dropwise. The mixture was stirred at room temperature for 2 hr, cooled at 0° C., mixed with water (2 mL), and extracted with ethyl acetate. The organic layer was dried over Na$_2$SO$_4$ and concentrated in vacuum. The crude product was purified by flash column chromatography on silica gel saturated with NH$_3$ eluting with hexane:ethyl acetate=1:1. Removal of the solvent gave 2d (14 mg, 20%); $[\alpha]_D^{22}=-124°$ (c=0.52, CHCl$_3$); IR (thin film) 3061, 2930, 2798, 1618, 1492, 941, 925 cm$^{-1}$; $^1$H NMR (CDCl$_3$, 300 MHz) δ7.23 (d, 2H, J=8.5 Hz), 7 (d, 2H, J=8.5 Hz), 6.14 (dd, 1H, J=13.4, 10 Hz), 5.47 (d, 1H, J=13.4 Hz), 3.27 (s, 1H), 3.03 (m, 2H), 2.28 (m, 1H), 2.22 (s, 3H), 2.18–1.64 (m, 6H); $^{13}$C NMR (CDCl$_3$, 75.46 MHz) 141.14, 133.88, 131.75, 129.34, 128.17, 117.55, 67.29, 61.99, 49.64, 41.96, 36.61, 34.50, 26.44, 24.98; mass spectrum, m/z 297 (M+, $^{37}$Cl), 195 (M+, $^{35}$Cl) 260, 218, 141, 97, 82.

EXAMPLE 9

3β-(Benzoyloxy)-2β-[(E)-2-(ethoxycarbonyl)vinyl]tropane (2e)

The aldehyde 4 prepared by Swern oxidation of 3 was reacted with (carboethoxymethylene) triphenylphosphorane in THF. After purification by silica gel chromatography, a solution of the α,β-unsaturated ester (42.3 mg, 0.12 mmol) in 3 mL of THF was treated with tetrabutylammonium fluoride trihydrate (TBAF·3H$_2$O) (79 mg, 0.25 mmol) at 25° C. for 4 hr. Water (5 mL) was added, and the mixture was extracted with CHCl$_3$ (4×10 mL). The combined organic layers were dried (MgSO$_4$) and concentrated. The residue was chromatographed on silica gel with MeOH as eluent to give the free alcohol (24.2 mg). This alcohol was dissolved in 2 mL of CH$_2$Cl$_2$, and to this solution was added 116 μL (1.0 mmol) of benzoyl chloride and 200 μL of triethylamine. After 15 hr at 25° C., saturated K$_2$CO$_3$ was added, and the mixture was extracted with CH$_2$Cl$_2$ (4×10 mL). The combined organic layers were dried over MgSO$_4$ and concentrated. The residue was chromatographed on silica gel with 50% ethyl acetate-hexane as eluent to give 2e (25.0 mg) as a pale yellow oil: IR (thin film) 2939, 1718, 1651, 1450, 1371, 1313, 1275, 1222, 1176, 1161, 1114, 1070, 1037, 985, 713, cm$^{-1}$; $^1$H NMR (CDCl$_3$) δ=1.25 (3H, t, J=7.5 Hz, COOEt), 1.73–1.78 (2H, m, 4-H) 1.92–2.17 (4H, m, 6-H, 7-H), 2.23 (3H, s, NMe), 2.88 (1H, m, 2-H) 3.15 (1H, br s, 5-H), 3.31 (1H, br s, 1H), 4.11–4.19 (2H, m, COOEt), 5.27 (1H, dr, J=12.0, 6.4, 6.4 Hz, 3-H) 5.82 (1H, d, J=15.8 Hz, =CHCOOEt), 7.35–7.44 (3H, m, CH=CHCOOEt and ArH), 7.49–7.54 (1H, m, ArH), 7.91–7.94 (2H, m, ArH); $^{13}$C NMR (CDCl$_3$) δ=14.22, 25.04, 26.13, 35.44, 41.03, 48.08, 60.05, 61.33, 66.68, 68.63, 122.87, 128.25, 129.51, 130.16, 132.88, 147.97, 165.85, 166.40; MS (m/z) 343 (M+), 298, 270, 248, 222, 154, 105, 82; $[α]_D = -15.1°$ C. (C=0. 113), $[α]_{578} = -15.1°$, $[α]_{546} = -16.9°$, $[α]_{436} = -21.3°$, $[α]_{365} = -35.6°$.

EXAMPLE 10

3β-Benzoyloxy-2β-[(E)-2-(diethoxyphosphono)vinyl]-tropane (2f)

Compound 2f was prepared in an identical fashion to ester 2e by simply substituting the anion prepared from (tetraethyl)methylenediphosphonate for the Wittig reagent used above. The resulting vinyl phosphonate was then treated sequentially with TBAF·3H$_2$O and PhCOCl as described in Example 7 to yield 2f: $[α]^{22}_D = 14.4°$ (c=0.355 g/100 mL, CHCl$_3$); IR (thin film) 2958, 2931, 1714, 1452, 1315, 1275, 1114, 1051, 1026, 1798, 715 cm$^{-1}$; $^1$H NMR (CDCl$_3$) δ=1.09, 1.21 (each 3H, t, J=7.1 Hz, P(OEt)$_2$), 1.65–1.70 (2H, m, H-6, H-7), 1.82–1.88 (1H, m), 1.99–2.12 (3H, m, H-6, H-7, H-4), 2.15 (3H, s, N-Me), 2.83–2.88 (1H, m, H-2), 3.05–3.08 (1H, m, H-5), 3.22 (1H, br s, H-1), 2.72–4.00 (4H, m, P(OEt)$_2$), 5.19 (1H, ddd, J=12.1, 6.8, 6.3 Hz, H-3), 5.59 (1H, dd, J=17.3, 21.6 Hz, =CH(P(OEt)$_2$), 7.17 (1H, ddd, J=2.19, 17.3, 9.4 Hz, CH=CHP(O)(O-Et)$_2$), 7.32–7.51 (3H, m, Ar), 7.91–7.93 (2H, m, Ar); $^{13}$C NMR (CDCl$_3$) δ16.17 (d, J$_{C-P}$=7.5 Hz), 25.05, 26.04, 29.58, 5.53, 41.11, 50.10 (d, J$_{C-P}$=22.1 Hz) 61.33, (d, J$_{C-P}$=7.9 Hz), 66.57, 68.85, 118.33 (d, J$_{C-P}$=184.7 Hz), 128.18, 29.47, 130.08, 132.86, 152.91, 165.67; MS (m/z) 407 (M+), 287, 286, 270 (base), 205, 148, 147, 123, 121, 105, 97, 94, 91, 83, 82, 81, 77, 76.

EXAMPLE 11

Drug Discrimination Studies

A. Training Protocols

Experimentally naive, male Sprague-Dawley rats (SASCO, Houston, Tex.) were trained to discriminate cocaine (10 mg/kg) from an equivalent volume (1 ml/kg) of saline (0.9% NaCl) using a standard two-lever, water-reinforced, FR 20 drug discrimination task. Drug or saline was administered intraperitoneally (IP) 15 min prior to daily (Monday-Friday) sessions. Rats (N=8) were trained first under a schedule of continuous water reinforcement (FR 1) with only the stimulus-appropriate (drug or saline) lever present ("errorless" training). The schedule of reinforcement was increased until all animals were responding reliably under a fixed ratio schedule for each experimental condition (FR 20). After responding in a stabilized fashion on an FR 20 schedule, both levers were presented simultaneously ("discrimination" training), and rats were required to respond on the stimulus-appropriate (correct) lever in order to obtain (water) reinforcement; there were no programmed consequences for responding on the incorrect lever. This phase of training continued until the performance of all animals attained criterion (individual mean accuracies of at least 80% correct prior to the first reinforcer for 10 consecutive sessions). After acquisition of the cocaine-discrimination, training sessions were shortened in length from 30 to 15 min.

B. Testing Protocols

Test sessions were initiated once all animals reached criterion (above) and were conducted 1 to 2 times per week in irregular order. Cocaine and saline sessions intervened between test sessions, to maintain discrimination accuracy. Only rats that met the 80% performance criteria during the preceding cocaine and saline sessions were tested. During test sessions, animals were placed in the chamber as during training sessions and upon completion of 20 responses on either lever or after the session time (20 min) had elapsed, a single (water) reinforcer was delivered, the house light was turned off, and the animals were removed from the chamber. After return to the home cages, all rats were allowed 10 to 15 min of free access to water. Two pharmacological test manipulations were performed during test sessions in substitution (generalization) tests, animals were tested for lever selection after the administration of various doses of the training drug or the challenge compound. In temporal (time course of drug action) tests, animals were injected with either cocaine (10 mg/kg) or various doses of the challenge drug and allowed to remain in their home cages for 5–240 min before generalization testing was conducted.

C. Data Analysis

During training sessions, accuracy was defined as the percentage of correct responses to total responses before the delivery of the first reinforcer; during test sessions, performance is expressed as the percentage of cocaine-appropriate responses to total responses prior to the delivery of the first reinforcer. Response rate (responses per min) is the total number of responses emitted before either 1) completion of 20 responses on the correct lever (training sessions) or 2) completion of 20 responses on either lever (test sessions), divided by the number of minutes to complete the first FR 20. A test compound was said to have substituted completely only when at least 80% of all responses occurred on the drug-appropriate lever; only data from animals that completed the FR 20 during test sessions were analyzed. Dose-response data were converted to a log-probit function, and least squares linear regression analyses were used to estimate the dose (milligrams per kilogram) of each agohist predicted to elicit 50% cocaine-appropriate responding (ED$_{50}$).

All publications, patents and patent applications are herein incorporated by reference to the same extent as if each individual publication, patent or patent application was specifically and individually indicated to be incorporated by reference.

It will be apparent to one of ordinary skill in the art that many changes and modifications can be made in the invention without-departing from the spirit or scope of the appended claims.

What is claimed is:

1. A compound of the formula:

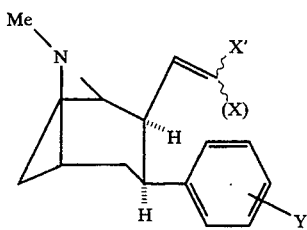

wherein X is H, halo, $(C_1-C_5)$alkyl, $(C_1-C_5)$alkoxy, $(C_1-C_5)$perfluoroalkyl, nitro, $(C_1-C_5)$alkoxycarbonyl, $(C_2-C_6)$acyl, $(C_2-C_6)$perfluoroacyl, azido, $Si(R)_3$, SR or $P(O)_2(OR)$, wherein R is H, $(C_1-C_5)$alkyl or $(C_6-C_{12})$aryl; Y is H, halo, $NO_2$, $(C_1-C_5)$ alkoxycarbonyl, carboxy, $(C_1-C_5)$alkyl, $(C_1-C_5)$alkoxy or $NR_2$, wherein each R is as defined above; and X' is H or $(C_1-C_5)$alkyl, wherein a waved line indicates a bond that is syn or anti to the $C_2$—CH= bond; and the pharmaceutically acceptable salts thereof.

2. The compound of claim 1 wherein X' is H.
3. The compound of claims 1 or 2 wherein X is H.
4. The compound of claims 1 or 2 wherein X is halo.
5. The compound of claim 4 wherein X is Cl.
6. The compound of claim 1 or 2 wherein Y is halo or H.
7. The compound of claim 6 wherein Y is para-Cl.
8. The compound of claims 1 or 2 wherein X is $(C_1-C_5)$alkoxycarbonyl.
9. The compound of claim 8 wherein X is methoxycarbonyl or ethoxycarbonyl.
10. The compound of claim 1 or 2 wherein X is $P(O)[O-(C_1-C_5)$alkyl $]_2$.
11. The compound of claim 10 wherein X is $P(O)(OMe)_2$.

* * * * *

UNITED STATES PATENT AND TRADEMARK OFFICE
CERTIFICATE OF CORRECTION

PATENT NO. : 5,391,744
DATED : February 21, 1995
INVENTOR(S) : Alan P. Kozikowski It is certified that error appears in the above-identified patent and that said Letters Patent is hereby corrected as shown below:

TITLE PAGE:
In References Cited-Publications, please insert --P.R. Andrews et al., J.Med.Chem., 27, 1648 (1984).--

In Column 1, line 7, after "BACKGROUND OF THE INVENTION" insert --This invention was made with the assistance of the U.S. Government under Grant No. DA 06856, awarded by the National Institute of Drug Abuse. The Government has certain rights in this invention.--

Column 8, line 68, delete "2drelative" and insert therefor --2d relative--.

Column 9, line 28, delete "6 units" and insert therefor --$\delta$ units--.

Column 13, line 41, delete "5.53" and insert therefor --35.53--.

Column 14, line 25, delete "sessions in substitution" and insert therefor --sessions. In substitution--.

Signed and Sealed this

Twenty-fourth Day of December, 1996

Attest:

BRUCE LEHMAN

*Attesting Officer*     *Commissioner of Patents and Trademarks*